(12) United States Patent
Clerc et al.

(10) Patent No.: US 6,860,900 B2
(45) Date of Patent: Mar. 1, 2005

(54) STENT AND STENT-GRAFT FOR TREATING BRANCHED VESSELS

(75) Inventors: Claude O. Clerc, Eden Prairie, MN (US); Paul F. Chouinard, Roseville, MN (US); Leonard Pinchuk, Miami, FL (US); Paul J. Thompson, New Hope, MN (US)

(73) Assignee: Schneider (USA) Inc., Plymouth, MN (US)

( * ) Notice: Subject to any disclaimer, the term of this patent is extended or adjusted under 35 U.S.C. 154(b) by 0 days.

(21) Appl. No.: 10/607,741

(22) Filed: Jun. 27, 2003

(65) Prior Publication Data

US 2004/0133266 A1 Jul. 8, 2004

Related U.S. Application Data

(63) Continuation of application No. 09/021,804, filed on Feb. 11, 1998, now abandoned.
(60) Provisional application No. 60/047,749, filed on May 27, 1997.

(51) Int. Cl.[7] .................................................. A61F 2/06
(52) U.S. Cl. ..................................... 623/1.35; 623/1.15
(58) Field of Search ................................ 623/1.13–1.2, 623/1.27, 1.35

(56) References Cited

U.S. PATENT DOCUMENTS

| 4,475,972 A | 10/1984 | Wong |
| 4,553,545 A | 11/1985 | Maass et al. |
| 4,655,771 A | 4/1987 | Wallsten |
| 4,732,152 A | 3/1988 | Wallsten et al. |
| 4,738,740 A | 4/1988 | Pinchuk et al. |
| 4,760,849 A | 8/1988 | Kropf |
| 4,771,773 A | 9/1988 | Kropf |
| 4,848,343 A | 7/1989 | Wallsten et al. |
| 4,850,999 A | 7/1989 | Planck |
| 4,875,480 A | 10/1989 | Imbert |
| 4,954,126 A | 9/1990 | Wallsten |
| 4,990,151 A | 2/1991 | Wallsten |

(List continued on next page.)

FOREIGN PATENT DOCUMENTS

| EP | 0 698 380 A1 | 2/1996 |
| EP | 0 775 472 A2 | 5/1997 |

*Primary Examiner*—Corrine McDermott
*Assistant Examiner*—Hieu Phan
(74) *Attorney, Agent, or Firm*—Ratner Prestia

(57) ABSTRACT

An implantable stent and stent-graft for treating a patient having a relatively healthy first aorta portion upstream from a renal artery branch, and a diseased aorta portion downstream from the renal artery branch. One embodiment of the device includes a fixation section, a renal artery branch section and a diseased aorta section, all of which can be tubular, radially compressible and self-expandable structures formed from a plurality of filaments which are helically wound in a braided configuration. When the device is implanted and in its expanded state, the fixation section engages the first aorta portion upstream from a renal artery branch to provide substantial anchoring support. The diseased aorta section engages the portion of the aorta downstream from the renal artery branch and extends across the diseased portion of the aorta for purposes of treatment. The renal artery branch section extends across the renal artery branch and connects the diseased aorta section to the fixation section while allowing blood flow between the aorta and renal artery branch.

16 Claims, 10 Drawing Sheets

U.S. PATENT DOCUMENTS

| | | |
|---|---|---|
| 5,019,090 A | 5/1991 | Pinchuk |
| 5,026,377 A | 6/1991 | Burton et al. |
| 5,061,275 A | 10/1991 | Wallsten et al. |
| 5,071,407 A | 12/1991 | Termin et al. |
| 5,084,065 A | 1/1992 | Weldon et al. |
| 5,092,877 A | 3/1992 | Pinchuk |
| 5,116,360 A | 5/1992 | Pinchuk et al. |
| 5,163,951 A | 11/1992 | Pinchuk et al. |
| 5,201,757 A | 4/1993 | Heyn et al. |
| 5,229,431 A | 7/1993 | Pinchuk |
| 5,356,423 A | 10/1994 | Tihon et al. |
| 5,405,380 A | 4/1995 | Gianotti et al. |
| 5,415,664 A | 5/1995 | Pinchuk |
| 5,464,408 A | 11/1995 | Duc |
| 5,484,444 A | 1/1996 | Braunschweiler et al. |
| 5,496,364 A | 3/1996 | Schmitt |
| 5,522,880 A | 6/1996 | Barone et al. |
| 5,534,287 A | 7/1996 | Lukic |
| 5,562,726 A | 10/1996 | Chuter |
| 5,575,817 A | 11/1996 | Martin |
| 5,575,818 A * | 11/1996 | Pinchuk .................... 623/1.15 |
| 5,591,172 A | 1/1997 | Bachmann et al. |
| 5,591,226 A | 1/1997 | Trerotola et al. |
| 5,591,228 A | 1/1997 | Edoga |
| 5,591,229 A | 1/1997 | Parodi |
| 5,607,466 A | 3/1997 | Imbert et al. |
| 5,628,787 A | 5/1997 | Mayer |
| 5,628,788 A | 5/1997 | Pinchuk |
| 5,632,772 A | 5/1997 | Alcime et al. |
| 5,639,278 A | 6/1997 | Dereume et al. |
| 5,645,559 A | 7/1997 | Hachtman et al. |
| 5,653,747 A | 8/1997 | Dereume |
| 5,662,703 A | 9/1997 | Yurek et al. |
| 5,667,486 A | 9/1997 | Mikulich et al. |
| 5,700,269 A | 12/1997 | Pinchuk et al. |
| 5,713,917 A | 2/1998 | Leonhardt et al. |
| 5,716,365 A | 2/1998 | Goicechea et al. |
| 5,718,159 A | 2/1998 | Thompson |
| 5,723,004 A | 3/1998 | Dereume et al. |
| 5,769,882 A | 6/1998 | Fogarty et al. |
| 5,800,519 A | 9/1998 | Sandrock |
| 5,868,783 A | 2/1999 | Tower |
| 5,935,161 A | 8/1999 | Robinson et al. |
| 6,102,940 A * | 8/2000 | Robichon et al. .......... 623/1.35 |
| 6,344,056 B1 | 2/2002 | Dehdashtian |

* cited by examiner

STENT AND STENT-GRAFT FOR TREATING BRANCHED VESSELS

REFERENCE TO RELATED APPLICATION

This application is a continuation application of application Ser. No. 09/021,804 now abandoned, filed Feb. 11, 1998 which claims the benefit of U.S. Provisional Application Ser. No. 60/047,749, filed May 27, 1997, and entitled "Bifurcated Stent Graft".

BACKGROUND OF THE INVENTION

1. Field of the Invention

The present invention is a radially self-expanding stent and stent-graft for treating bifurcated and other branched vessels of a patient, and methods for manufacturing and implanting the stent and stent-graft.

2. Description of the Related Art

Medical prostheses frequently referred to as stents and stent-grafts are well known and; commercially available. These devices are used within body vessels of humans and other animals for a variety, of medical applications. Stents and stent-grafts are, for example, used to repair (i.e., treat) abdominal aortic aneurysms. An abdominal aortic aneurysm is an enlarged (i.e., dilated) and weakened diseased area of the portion of the aorta between the renal artery branch (i.e., the location at which the renal arteries meet the aorta) and the iliac bifurcation (i.e., the location downstream from the renal artery, branch at which the aorta branches or divides into the iliac arteries). Stenosis, a narrowing and occlusion of the aorta typically caused by tissue buildup, also is often present at these aneurysms. Aneurysms and stenosis at the carotid artery bifurcation (i.e., the location at which the common carotid artery branches into the internal carotid artery and the external carotid artery) are also treated with stents and stent-grafts.

The Parodi U.S. Pat. No. 5,591,229 is directed to an aortic graft for repairing an abdominal aortic aneurysm. Briefly, the graft includes an elongated tube having first and second ends, and securing means for securing the first end of the tube to the aorta. The securing means is an expandable thin-walled member with a plurality of slots parallel to the longitudinal axis of the member. The thin-walled member is configured for delivery in an unexpanded and undeformed diameter state with an inflatable balloon within the member. After being intraluminally delivered to the site of the aneurysm, the balloon is inflated to radially extend the thin-walled member to an expanded and deformed diameter state. The first end of the thin-walled member is thereby secured to the aorta. Deflation of the balloon causes it to be disengaged from the thin-walled member and permits its withdrawal.

A graft for treating an aneurysm which extends above the renal arteries is shown in FIG. 7 of the Parodi patent. This graft includes a thin-walled securing member which is interconnected to the tube by at least one flexible connector member. The flexible connector member spans the part of the aorta adjacent the renal arteries so that blood flow through the renal arteries is not obstructed. There remains, however, a continuing need for stents and stent-grafts for treating branched vessels. Improved stents and stent-grafts for treating abdominal aortic aneurysms and/or stenosis at the carotid artery bifurcation would be especially useful. For example, stents and stent-grafts capable of remaining fixed vessel as the diseased area of the vessel expands would be desirable. Since accurately positioning a stent and stent-graft in a branched vessel can be challenging, a device of this type that can be relatively easily repositioned would also be desirable. In general, stents and stent-grafts having different characteristics enable medical personnel to select a device most suitable for the treatment of the particular indication of the patient.

SUMMARY OF THE INVENTION

The present invention is an implantable medical device for treating a portion of a patient's vessel having a branch a first portion upstream from the branch, and a second portion downstream from the branch. One embodiment of the device includes a first or upstream section, a second or downstream section and a branch section. The upstream section has a first porosity and comprises a plurality filaments which are helically wound and interwoven in a braided configuration to form a tubular, radially compressible and self-expandable structure. The upstream section engages the first portion of the vessel upstream from the branch when in an expanded state. The downstream section has a second porosity and comprises a plurality filaments which are helically wound and interwoven in a braided configuration to form a tubular, radially compressible and self-expandable structure. The downstream section engages the downstream portion of the vessel downstream from the branch when in an expanded state. The branch section has a third porosity which is greater than at least one of the first and second porosities, and comprises a radially compressible and expandable structure. When implanted, the branch section extends across the branch to connect the upstream and downstream sections while allowing blood flow from the first portion of the vessel to the branch. The device can be used to efficaciously treat indications such as aneurysms in the abdominal aorta and stenosis near the carotid artery bifurcation.

DETAILED DESCRIPTION OF THE PREFERRED EMBODIMENTS

Figure 1:
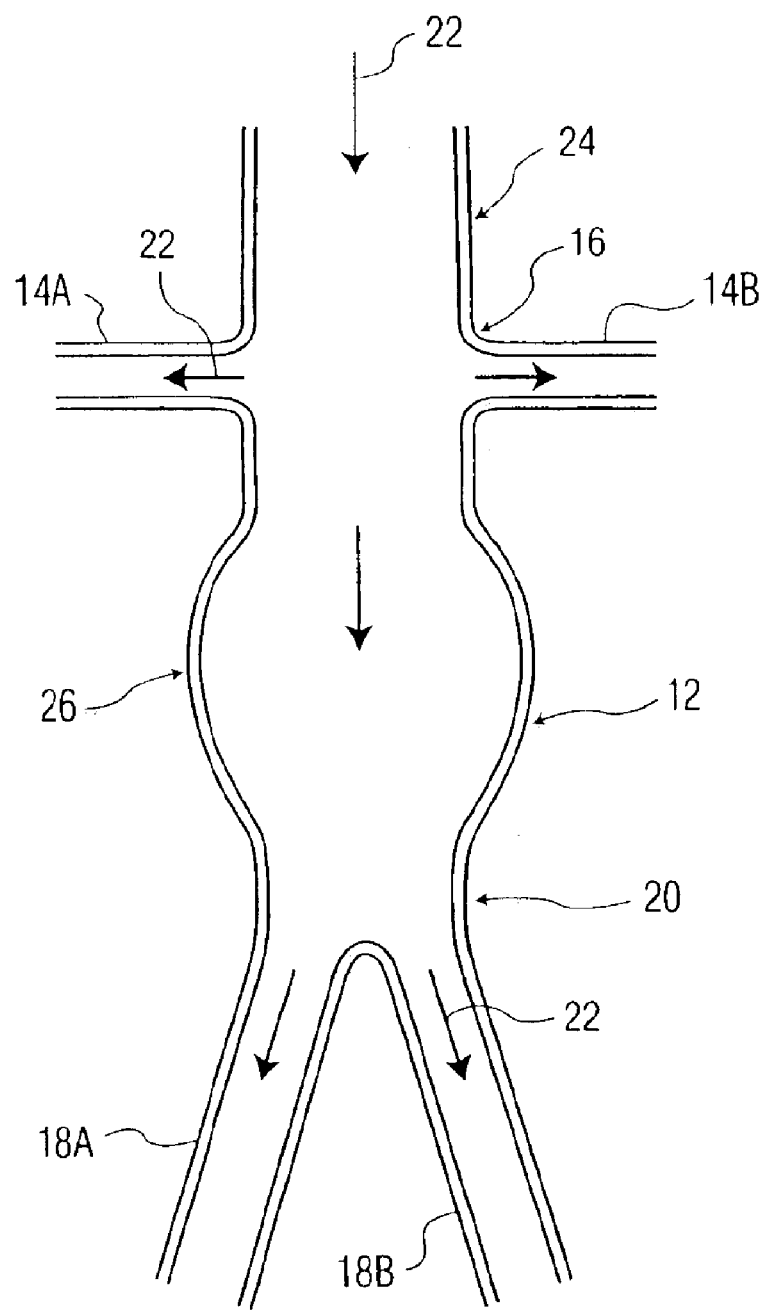
FIG. 1 is an illustration of a portion of an aorta in which stents and stent-grafts in accordance with the present invention can be implanted.

FIG. 1 is an illustration of a section of a diseased abdominal aorta 12 which can be treated by the aortic stent and stent-graft of the present invention. As shown, renal arteries 14A and 14B extend from the aorta 12 at renal artery branch 16. Downstream from (i.e., on a first side of) the renal artery branch 16 is the iliac bifurcation 20 at which the aorta 12 divides (i.e., branches) into iliac arteries 18A and 18B. The stent and stent-graft of the present invention can be used to treat a diseased portion 26 of the aorta 12 which is located between the renal artery branch 16 and the iliac bifurcation 20. The diseased portion 26 is represented in FIG. 1 by an aneurysm (i.e., a weakened and expanded-diameter section). Although not shown in FIG. 1, the aneurysm or other disease attributes (i.e., indications) of the aorta 12 being treated can extend all the way to the renal arteries 14A and 14B, and/or beyond the iliac bifurcation 20 into the iliac arteries 18A and/or 18B. As described in greater detail below the stent and stent-graft of the present invention can make use of a portion 24 of the aorta 12 which is typically relatively healthy, and located upstream from the renal artery branch 16 (i.e., on a second side of the renal artery branch and opposite the branch from the diseased portion 26). Arrows 22 are included in FIG. 1 to illustrate the direction of blood flow through the aorta 12, renal arteries 14A and 14B and iliac arteries 18A and 18B.

Figure 2:
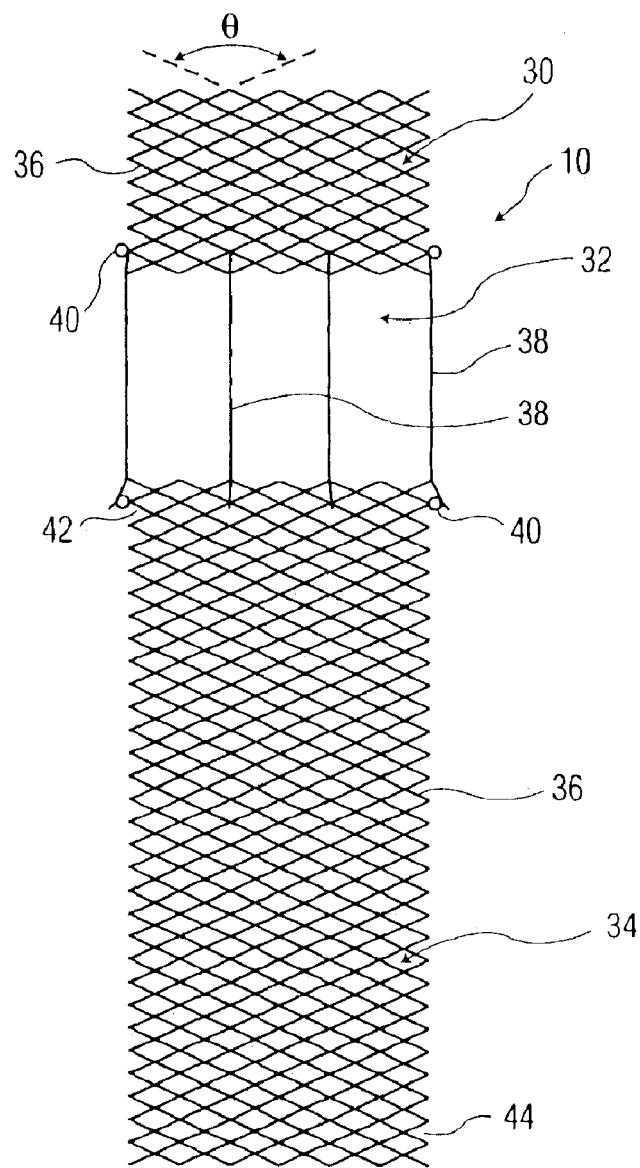
FIG. 2 is an illustration of a stent in accordance with a first embodiment of the present invention.

Aortic stent 10, a first embodiment of the present invention, is shown in FIG. 2. Stent 10 is a tubular device and includes an upstream or fixation section 30, renal artery branch section 32 and downstream or diseased aorta section 34. Fixation section 30 and diseased aorta section 34 are formed from two sets of oppositely-directed, parallel, spaced-apart and helically wound elongated strands or filaments 36. The sets of filaments 36 are interwoven in an over and under braided configuration intersecting at points to form an open mesh or weave construction. Methods for fabricating stent structures such as fixation section 30 and diseased aorta section 34 are generally known and disclosed, for example, in the Wallsten U.S. Pat. No. 4,655,771 and the Wallsten et al. U.S. Pat. No. 5,061,275, which are hereby incorporated by reference in their entirety for all purposes. In the embodiment of stent 10 shown in FIG. 2, the fixation section 30 and diseased aorta section 34 are formed from structures which are substantially similar with the exception of their length. Other embodiments of the invention described below include fixation and diseased aorta sections which are formed from stent structures having different characteristics.

Figure 3:
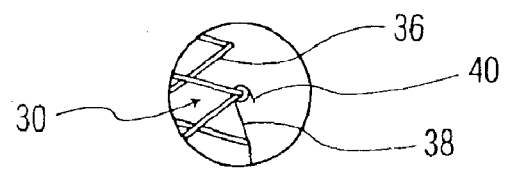
FIG. 3 is a detailed illustration of a portion of the stent shown in FIG. 2, showing one of the filaments of the renal artery branch section wound around a filament of the fixation section.

Renal artery branch section 32 is formed by filaments 38 which have their opposite ends 40 connected to filaments 36 of the fixation section 30 and diseased aorta section 34. Six filaments 38 (only four, are visible) which are parallel to the longitudinal axis and equally spaced around the circumference of the stent 10 are shown in FIG. 2. As perhaps best shown in FIG. 3, the opposite ends 40 of the filaments 38 are connected to the fixation section 30 and diseased aorta section 34 by being wound around the filaments 36 of the fixation and diseased aorta sections. The ends 40 of the wound filaments 38 can extend at an acute angle with respect to a longitudinal axis of the stent 10, and toward the diseased aorta section 34, to form a barb which can help anchor the stent 10 to the aorta 12 or other vessel in which the stent is implanted. In other embodiments (not shown) the filaments 38 of the renal artery branch section 32 can be attached to the fixation section 30 and diseased aorta section 34 by other known or methods such as welding. As is evident from FIG. 2, the porosity of the renal artery branch section 32 is greater that that of the fixation section 30 and the diseased aorta section 34 (i.e., the density of the filaments 36 in the fixation and diseased aorta sections is greater than the density of the filaments 30 in the renal artery branch section).

Stent 10 is shown in its expanded or relaxed state in FIG. 2, i.e., in the configuration it assumes when subjected to no external loads or stresses. The filaments 36 are resilient, permitting the radial compression of the fixation section 30 and diseased aorta section 34 of stent 10 into a reduced-radius, extended-length configuration or state. The renal artery branch section 32 can also be radially compressed into a reduced-radius configuration or state along with the fixation section 30 and diseased aorta section 34, thereby rendering the stent 10 suitable for delivery to the diseased aorta treatment site through a body vessel (i.e., transluminally). Stent 10 is also self-expandable from the compressed state, and axially flexible.

A wide variety of materials can be used for the self-expanding stent filaments 36 and 38. Commonly used materials include Elgiloy® and Phynox® spring alloys. Elgiloy® alloy is available from Carpenter Technology Corporation of Reading Pa. Phynox® alloy is available from Metal Imphy of Imphy, France. Other materials used for self-expanding stent filaments 36 and 38 are 316 stainless steel and MP35N alloy which are available from Carpenter Technology Corporation and Latrobe Steel Company of Latrobe, Pa., and superelastic Nitinol alloy which is available from Shape Memory Applications of Santa Clara, Calif.

Conventional or otherwise known devices for delivering self-expanding stents can be used to deliver stent 10 to a diseased aorta 12. Delivery devices of these types are, for example, disclosed in the Wallsten et al. U.S. Pat. No. 4,732,152, Burton et al. U.S. Pat. No. 5,026,377, Heyn et al. U.S. Pat. No. 5,201,757, and Braunschweiler et al. U.S. Pat. No. 5,484,444. Briefly, the delivery devices (not shown) can include an elongated and flexible inner tube having proximal and distal ends. The stent 10 is forced into its reduced-radius compressed state around the distal end of the inner tube, and constrained in the compressed state by an outer tube which surrounds the inner tube and stent 10. A deployment mechanism which can be actuated from the proximal end of the delivery device retracts the outer tube with respect to the inner tube, thereby allowing the stent 10 to self-expand into engagement with the inner wall of the aorta 12.

Figure 4:
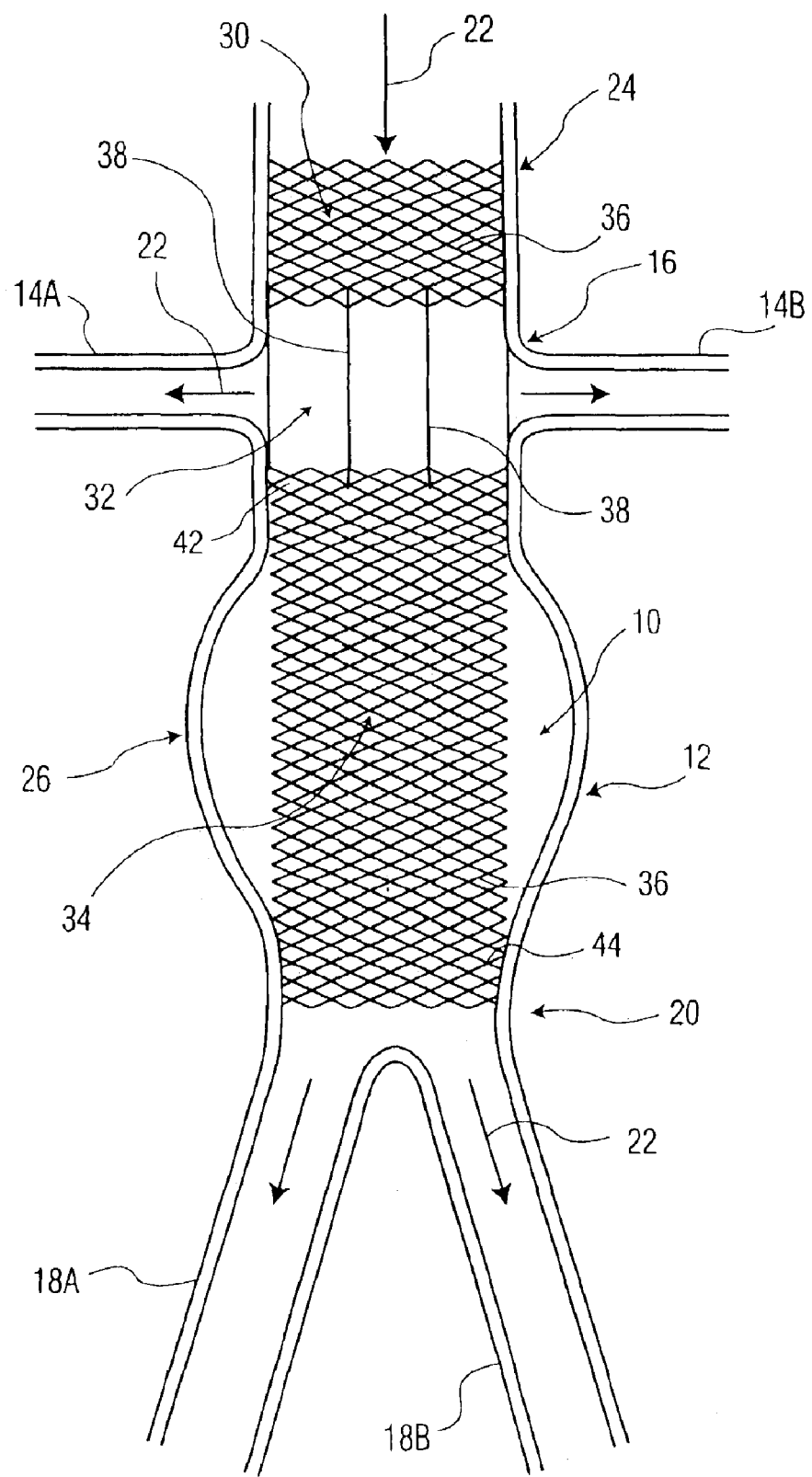
FIG. 4 is an illustration of the stent shown in FIG. 2 after implantation in the portion of the aorta shown in FIG. 1.

The assembled delivery device is inserted percutaneously into the femoral artery and directed through the artery until the distal end with the constrained stent 10 is positioned at the diseased portion 26 of the aorta 12. The deployment mechanism is then actuated to allow the stent 10 to self-expand into engagement with the aorta 12. FIG. 4 is an illustration of the stent 10 implanted into the aorta 12 shown in FIG. 1. As shown, fixation section 30 is located at and engaged with the relatively healthy portion 24 of the aorta 12 immediately opposite the renal arteries 14A and 14B from the iliac branch 20. Renal artery branch section 32 is located at the renal artery branch 16 and extends across the locations at which the renal arteries 14A and 14B open into the aorta 12. The diseased aorta section 34 of the stent 10 extends across the diseased portion 26 of the aorta 12, and therefore provides additional strength for this vessel. In a similar manner, the support provided by diseased aorta section 34 can help maintain a diseased aorta open in the presence of stenosis (not shown in FIGS. 1 and 2) which would otherwise reduce the blood flow capabilities of the vessel.

In the embodiment shown in FIG. 4, the diseased aorta section 34 of stent 10 extends from a location immediately downstream from the renal arteries 14A and 14B to a location immediately adjacent to the iliac arteries 18A and 18B. A first end 42 of the diseased aorta section 34 adjacent to the renal artery branch section 32 is expanded radially outwardly into engagement with the inner walls of the aorta 12 adjacent to the renal arteries 14A and 14B. A second end 44 of the diseased aorta section 36 is expanded radially outwardly into engagement with the inner walls of the aorta 12 adjacent to the location at which the iliac arteries 108A and 18B intersect the aorta. As shown, the diseased portion 26 of aorta 12 between the portions at which ends 42 and 44 of the section 34 engage the aorta (i.e., the aneurysm) is weakened and extends outwardly beyond the stent 10. Under this and other similar conditions the amount of anchoring support provided by the relatively small surface area engagement of the ends 42 and 44 with the diseased portion 26 of the aorta 12 may not be sufficient to securely maintain the stent section 34 in its implanted position.

Fixation section 30 of the stent 10, through its engagement with the relatively healthy portion 24 of the aorta 12 and its interconnection to the diseased aorta section 34 by filaments 38, provides substantial anchoring support for the diseased aorta section. The fixation section 30 thereby enhances the positional stability of the implanted diseased aorta section 34. This enhanced positional stability is achieved without substantially restricting blood flow to the renal arteries 14A and 14B since the material density of the renal artery branch section, 34 (i.e., the density of filaments 38 of stent 10) is relatively low. As used in this document, the term "porosity" also refers to the density or spacing of the filaments 38 (e.g., the amount of open space between the filaments with respect to the amount of space occupied by the filaments). Additional anchoring support for the stent 10 is provided by the barbed-type ends 40 of filaments 38 which engage the interior wall of the aorta 12.

A stent 10 for implantation in the aorta 12 of an average size adult patient can be between about 5 cm and 15 cm in length, and have an expanded state diameter between about 2 cm and 5 cm. The fixation section 30 can be between about 1 cm and 5 cm in length. The renal artery branch section 32 can be between about 1 cm and 5 cm in length. The diseased aorta section 34 can be between about 4 cm and 15 cm in length. These dimensional ranges can of course be larger and smaller to accommodate the anatomy of larger and smaller patients.

Features and characteristics of the fixation section 30 can be varied to change the amount of anchoring support being provided. For example, the amount of anchoring support will increase with increasing length of the fixation section 30 (due to increased surface area of engagement), with increasing braid angle θ of filaments 36 (illustrated in FIG. 2, due to increased radial force generated by the section), and with increasing diameter (e.g., an outwardly flared end) and/or stiffness of filaments 36 (due to increased radial force of the section). Conversely, these and other characteristics of the fixation section can be decreased or otherwise varied to decrease the amount of anchoring support provided by the fixation section 30. The force exerted by the fixation section 30 on the aorta, and therefore the amount of anchoring support being provided, is the summation of the radial pressure exerted over the surface area of the section. The amount of anchoring support can therefore be varied by changing the radial pressure and surface area characteristics of the fixation section 30.

The amount of anchoring support to be provided by the fixation section 30, and the features and characteristics of the fixation section to provide the support, can be optimized and selected to suit the indications of the particular diseased aorta 12 in which the stent 10 is to be implanted. For example, the relative amount of anchoring support to be provided by the fixation section 30 will often depend upon the amount of positional support that the diseased aorta section 34 is capable of generating in connection with the aorta 12 in which it is implanted. In the example shown in FIG. 4, for example, the diseased aorta section 34 generates at least some anchoring support where its ends 42 and 44 engage the aorta 12. Diseased aortas that are relatively more or less healthy than that shown at 12 in FIG. 4 may be suitable for use with stents 10 having a fixation section 30 which provides less or more anchoring support, respectively, than the fixation section shown in FIG. 4. The manner by which the fixation section 30 is configured to provide the desired amount of anchoring support can depend on the nature (e.g., relative health) of the portion 24 of the aorta 12 in which the fixation section is to be implanted. For example, if the portion 24 of aorta 12 in which the fixation section 30 is to be implanted is relatively weak, it may be advantageous to provide a fixation section which generates relatively low radial forces, but which is relatively long to achieve the desired anchoring support.

Figure 5:
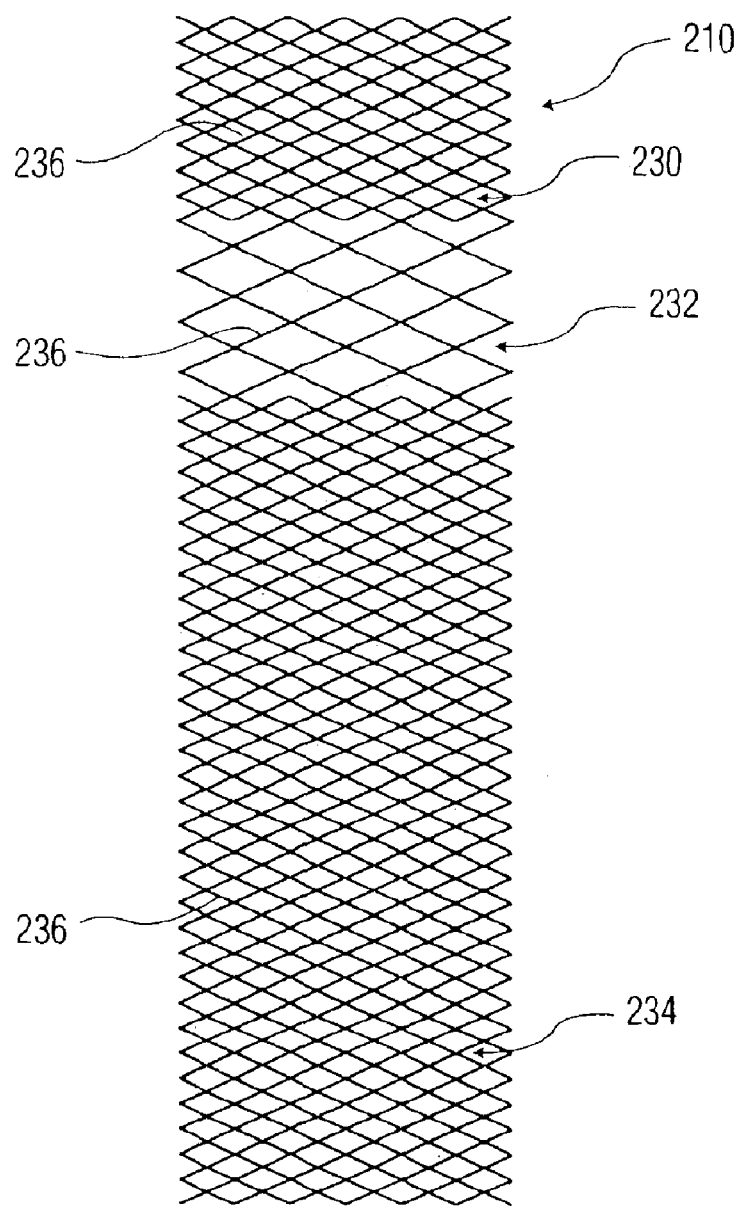
FIG. 5 is an illustration of a stent in accordance with a second embodiment of the present invention.

Stent 210, a second embodiment of the present invention, is illustrated in FIG. 5. Features of stent 210 which are similar to those of stent 10 shown in FIG. 2 are indicated by like reference numbers, and have similar characteristics. As shown, the stent 210 includes fixation section 230, renal artery branch section 232 and diseased aorta section 234. Sections 230, 232 and 234 are all formed from self-expanding, braided filament stent structures of the type described above. Stent 210 can be manufactured from a unitary braided filament stent structure by cutting and removing selected filaments from the portion of the structure to form the renal artery branch section 232. The density of the braided filaments 236 in the renal artery branch section 232 is thereby reduced from the density of the filaments in the fixation section 230 and the diseased aorta section 234. By way of example, stents such as 210 can be formed from thirty-eight to ninety-six filaments 236 (each of which is an individual, wire and/or a pair of wires), with fifty to seventy-five percent of these filaments being cut and removed from the original structure to form the renal artery branch section 232. Stent 210 can be implanted in a manner similar to that of stent 10 and described above.

Figure 6:
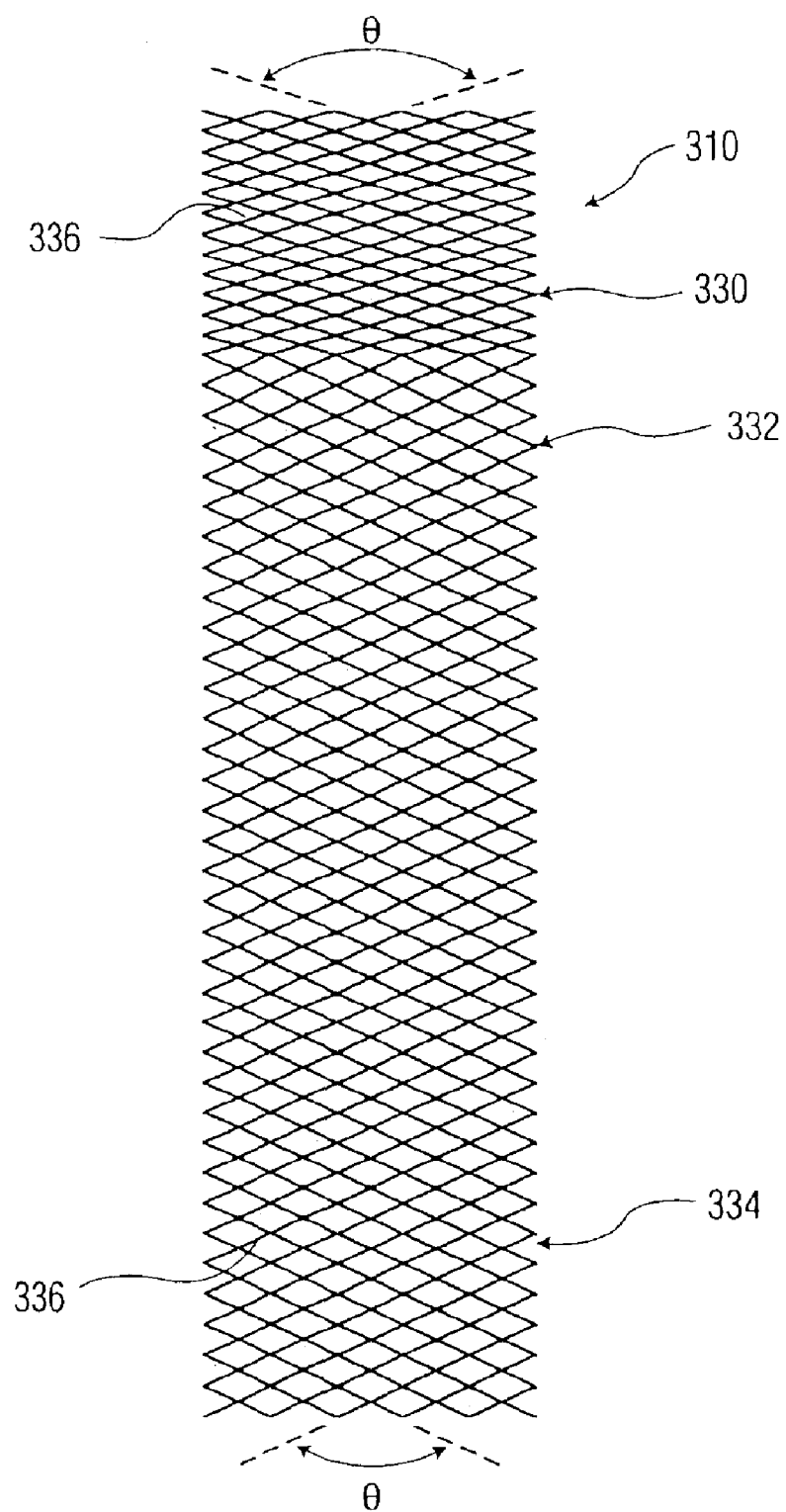
FIG. 6 is an illustration of a stent in accordance with a third embodiment of the present invention.

Stent 310, a third embodiment of the present invention, is illustrated in FIG. 6. Features of stent 310 which are similar to those of stent 10 shown in FIG. 2 are indicated by like reference numbers, and will have similar characteristics. As shown, the stent 310 includes fixation section 330, renal artery branch section 332 and diseased aorta section 334. Sections 330, 332 and 334 are all formed from self-expanding, braided filament stent structures of the type described above. The braid angle θ of the filaments 336 (and therefore the density and radial force) of the fixation section 330 is greater than the braid angle θ of the filaments in the renal artery branch section 332 and the diseased aorta section 334; In the embodiment shown, the braid angle θ of the filaments 336 in the renal artery branch section 332 and the diseased aorta section 334 are substantially similar. Stent 310 can be manufactured as a unitary braided filament structure by changing the braid angle during manufacture at the location corresponding to the intersection of the renal artery branch section 332 and the fixation section 330. The braid angle can also be changed by changing the braiding mandrel diameter, and by heat treating the stent at a given diameter. Stent 310 can be implanted in a patient in a manner similar to that of stent 10 and described above.

Figure 7:
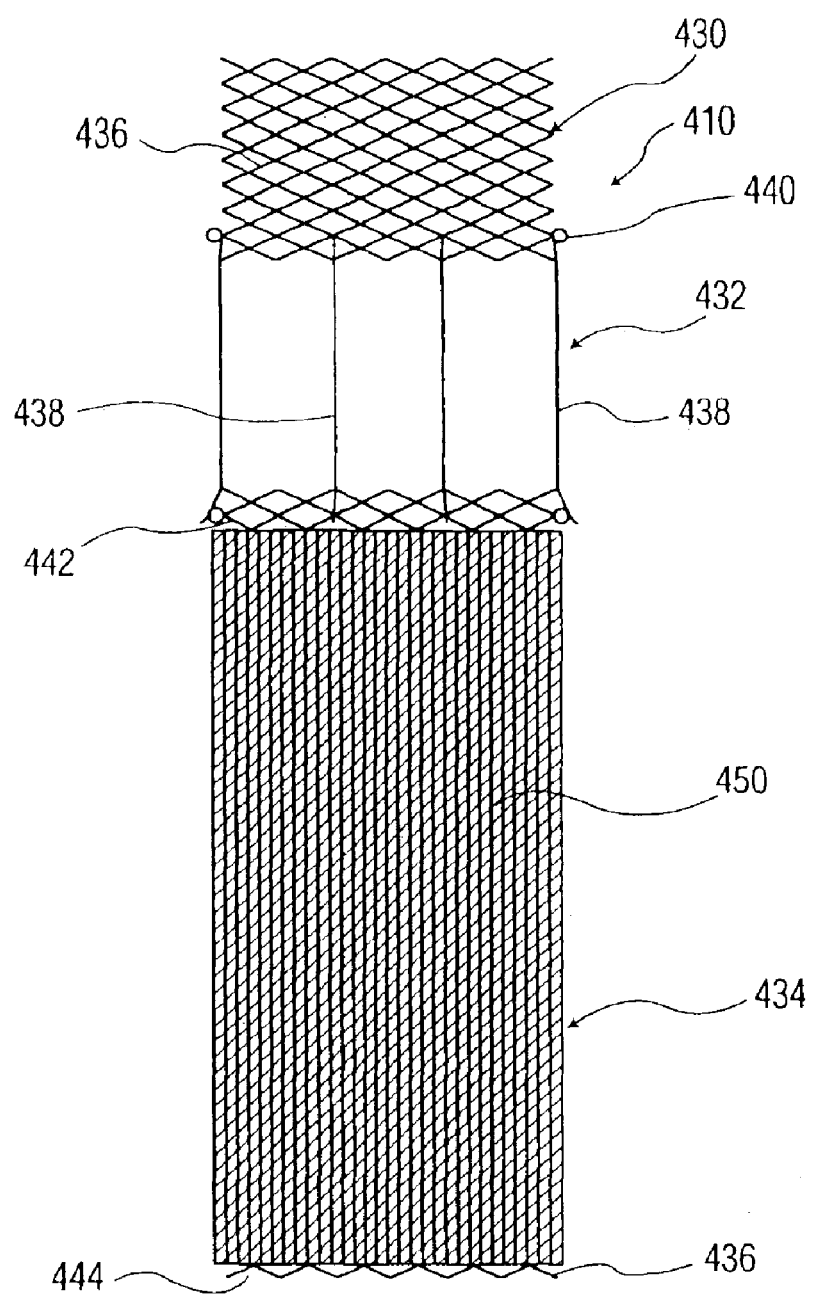
FIG. 7 is an illustration of a stent-graft in accordance with a fourth embodiment of the present invention.

Stent-graft 410, a fourth embodiment of the present invention, is illustrated in FIG. 7. Many features of stent-graft 410, and in particular fixation section 430 and renal artery branch section 432, are similar to those of stent 10 described above, are indicated by like reference numbers, and will have similar characteristics. A primary difference between stent 10 and stent-graft 410 is that the stent-graft includes a tubular graft cover 450 incorporated on the diseased aorta section 434. The illustrated embodiment of stent-graft 410 includes a diseased aorta section 434 formed from a braided filament stent structure of the type described above with reference to stent 10, and a separately fabricated graft cover 450 which is attached to the stent structure by adhesive, thread or filament stitching or other conventional techniques. The braided filament stent structure provides the radially self-expandable features and characteristics described above, and thereby effectively functions as a support structure. The tubular graft cover 450 effectively functions as a blood flow-shunting lumen, thereby supplementing the functionality of the portion of the aorta 12 in which the diseased aorta section 434 is implanted. The tubular graft cover 450 is flexible and radially collapsible. When the braided filament stent structure is in its reduced-radius, compressed state, the graft cover 450 collapses enabling the stent-graft 410 to be mounted on a deployment mechanism in the manner described above. The graft cover 450 is forced into and supported in its tubular, blood flow-shunting shape by the braided filament stent structure when the stent-graft 410 is deployed.

Graft cover 450 can be any of a variety of structures which have the characteristics described above (e.g., are flexible and radially collapsible) and which are sufficiently non-porous to shunt blood flow. Graft cover 450 can, for example, be formed from relatively tightly braided filaments of polymers such as polyethylene, polyethelyne terephalate and polyester. One suitable high molecular weight polyethylene is sold under the brand name "Spectra." A suitable PET material is commercially available under the brand name "Dacron." Alternatively, graft cover 450 can be formed from a sheet of material which is either itself impervious to blood flow, or covered with a coating which renders the material impervious. In still other embodiments graft cover 450 is a film, sheet or tube of biocompatible material such as ePTFE.

Other embodiments of graft cover 450 are formed by winding or spinning an extruded fiber onto a mandrel. Materials and methods for manufacturing graft covers 450 of these types are, described in the following U.S. Patents, all of which are hereby incorporated by reference in their entirety Wong, U.S. Pat. No. 4,475,972, Pinchuk et al., U.S. Pat. No. 4,738,740; Pinchuk, U.S. Pat. No. 5,229,431; and Dereum, U.S. Pat. No. 5,653,747.

Yet other embodiments of stent-graft 410 (not shown) include a diseased aorta section 434 in which the graft cover 450 is formed by multiple textile strands which are interbraided with each other and the filaments 436 of the stent structure to effectively form a composite stent and graft cover structure. Structures of these types which can be incorporated into stent-graft 410, and associated methods of manufacture, are described in European Patent Publication EP 0 804 934, and commonly assigned U.S. application Ser. No. 08/640,062, filed Apr. 30, 1996, Ser. No. 08/640,091, filed Apr. 30, 1996, Ser. No. 08/946,906, filed Oct. 8, 1997, and Ser. No. 08/988,725, filed Dec. 11, 1997, all of which are hereby incorporated by reference in their entirety.

Figure 8:
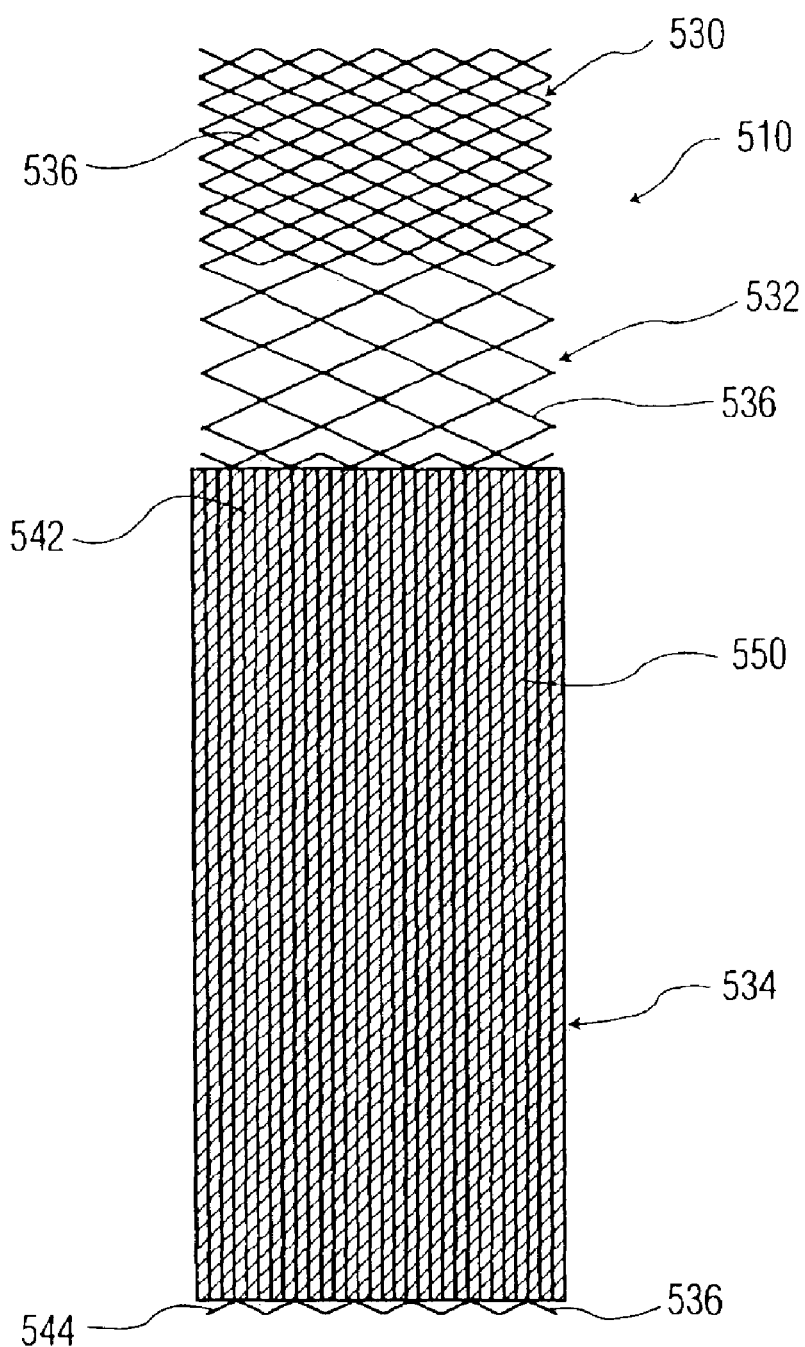
FIG. 8 is an illustration of a stent-graft in accordance with a fifth embodiment of the present invention.

Stent-graft 510, a fifth embodiment of the present invention is illustrated in FIG. 8. Fixation section 530, renal artery branch section 532 and the braided filament stent structure of the diseased, aorta section 534 are similar in structure and characteristics to those of stent 210 described above, and are indicated by like reference numbers. The graft cover 550 of stent-graft 510 can be similar in structure and characteristics to that of graft cover 450 of stent graft 410 described above. The graft cover 550 can be incorporated on the diseased aorta section 534 in a manner similar to the manner described above by which graft cover 450 is incorporated on the diseased aorta section 434 of stent-graft 410.

Figure 9:
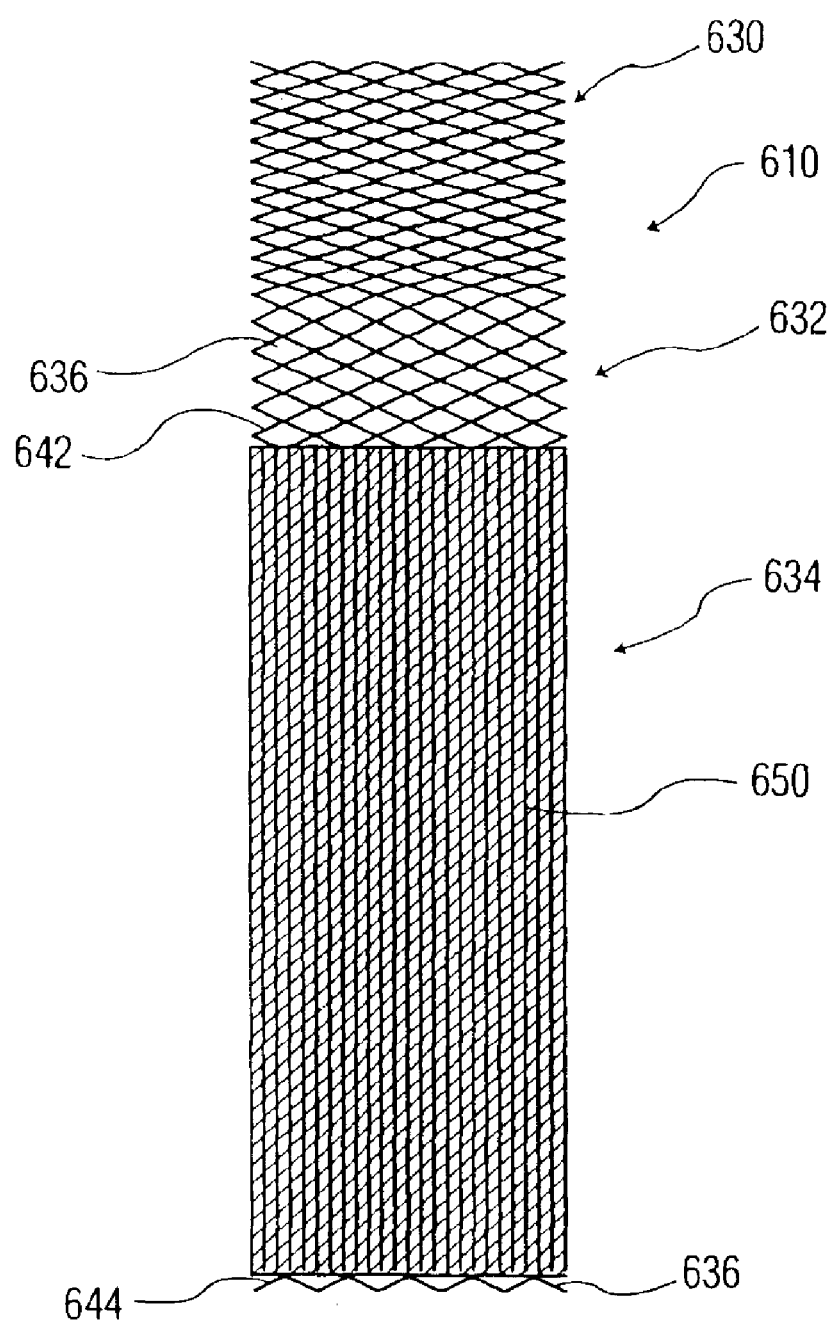
FIG. 9 is an illustration of a stent-graft in accordance with a sixth embodiment of the present invention.

Stent-graft 610, a sixth embodiment of the present invention, is illustrated in FIG. 9. Fixation section 630, renal artery branch section 632 and the braided filament stent structure of the diseased aorta section 634 are similar in structure and characteristics to those of stent 310 described above, and are indicated by like reference numbers. The graft cover 650 of stent-graft 610 can be similar in structure and characteristics to that of graft cover 450 of stent-graft 410 described above. The graft cover 650, can be incorporated on the diseased aorta section 634 in a manner similar to the manner described above by which graft cover 450 is incorporated on the diseased aorta section 434 of stent-graft 410.

Stent-grafts 430, 530 and 630 described above all include a tubular diseased aorta section 434, 534 and 634, respectively. Other embodiments of the invention (not shown) include bifurcated diseased aorta sections. Self-expanding bifurcated stent-grafts are, for example, described in the Alcime et al. U.S. Pat. No. 5,632,772, the Dereume et al. U.S. Pat. No. 5,639,278 and the Thompson and Du U.S. patent application Ser. No. 60/047,749 entitled "Bifurcated Stent rabt." Bifurcated stent-grafts of these types can be used for indications in which the aortic aneurysm extends to the iliac bifurcation 20 (FIG. 1), or beyond the iliac bifurcation and into one or both of the iliac arteries 18A and 18B. Still other embodiments of the invention (also not shown) include an aorto-monoiliac diseased aorta section. Aorto-monoiliac stent-grafts of these types are used in connection with femoro-femoral bypass surgical procedures.

Figure 10:
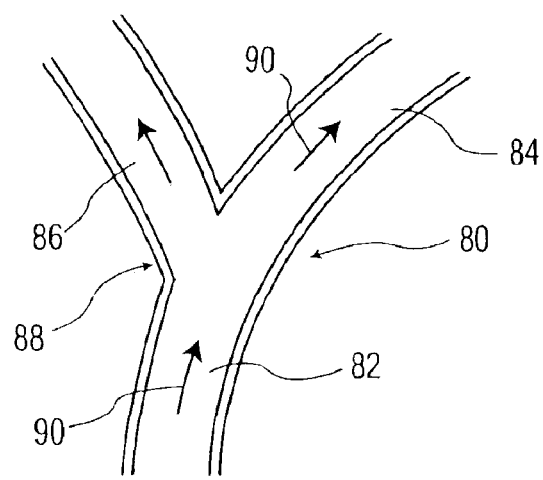
FIG. 10 is an illustration of a portion of a carotid artery in which stents and stent-grafts in accordance with the present invention can be implanted.

FIG. 10 is an illustration of a portion of a carotid artery 80 which can be treated by the stent and stent-graft of the present invention. As shown, the common carotid artery 82 divides into the internal carotid artery 84 and the external carotid artery 86 at the branch or bifurcation 88. The stent and stent-graft of the present invention are configured to treat a diseased portion of carotid artery 80 which is located adjacent to the bifurcation 88. Often, the diseased portion of carotid artery 80 will include a section of the common carotid artery 82 immediately upstream from the bifurcation 88 and a portion of at least one of the internal carotid artery, 84 and the external carotid artery 86 immediately downstream from the bifurcation. Arrows 90 are included in FIG. 10 to illustrate the direction of blood flow through the common carotid artery 82 (an upstream portion) and the internal and external carotid arteries 84 and 86, respectively (downstream portions).

Figure 11:
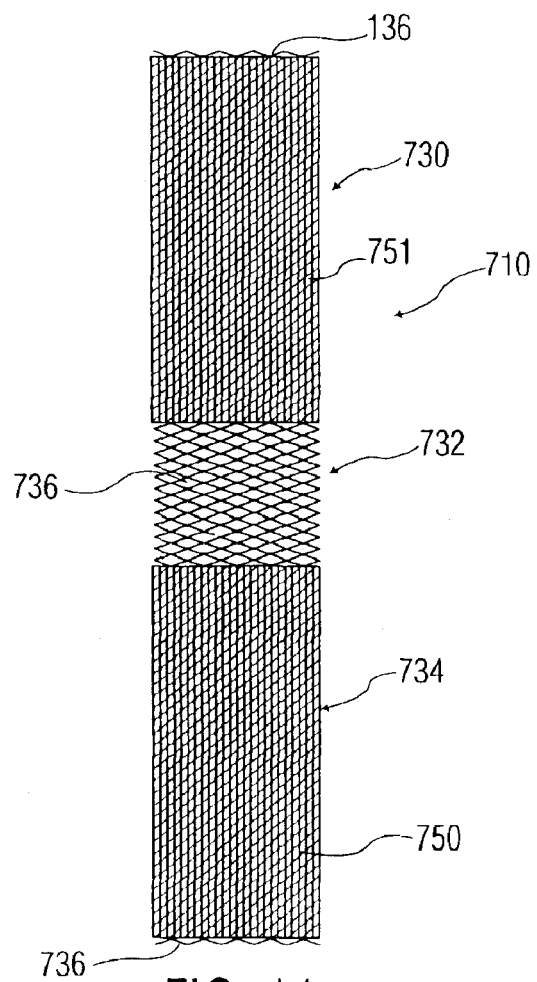
FIG. 11 is an illustration of a stent-graft in accordance with a seventh embodiment of the present invention.

Stent-graft 710, a seventh embodiment of the present invention, is illustrated in FIG. 11. As shown stent-graft 710 includes an upstream section 730, a branch section 732 and a downstream section 734. The braided filament stent structures of stent-graft sections 730, 732 and 734 can be portions of a unitary braided filament stent structure such as those described above, and are similar in structure and characteristics. In a manner similar to that of the fixation section 30 of stent 10 described above, the features and characteristics of the braided filament stent structures of upstream section 730 and/or downstream section 734 can be varied to change the amount of anchoring support being provided by these sections.

Graft covers 750, and 751 are incorporated into the downstream section 734, and upstream section 730, respectively, of the stent-graft 710. The downstream section graft cover 750 and upstream section graft cover 751 can be similar in structure and characteristics to those of graft cover 450 of stent-graft 410 described above. These graft covers 750 and 751 have a relatively low porosity (i.e., are microporous), so they substantially prevent fluid flow after coagulation, but allow the exchange of nutrients. The graft covers 750 and 751 also can be incorporated on the upstream section 730 and downstream section 734 in a manner similar to the manner described above by which the graft cover 450 is incorporated on the section 434 of stent-graft 410. Since the graft covers 750 and 751 have a relatively low porosity, the porosity of the interwoven filaments 736 of the branch section 732 will be relatively high with respect to the porosity of the downstream section 734 and upstream section 730.

Figure 12:
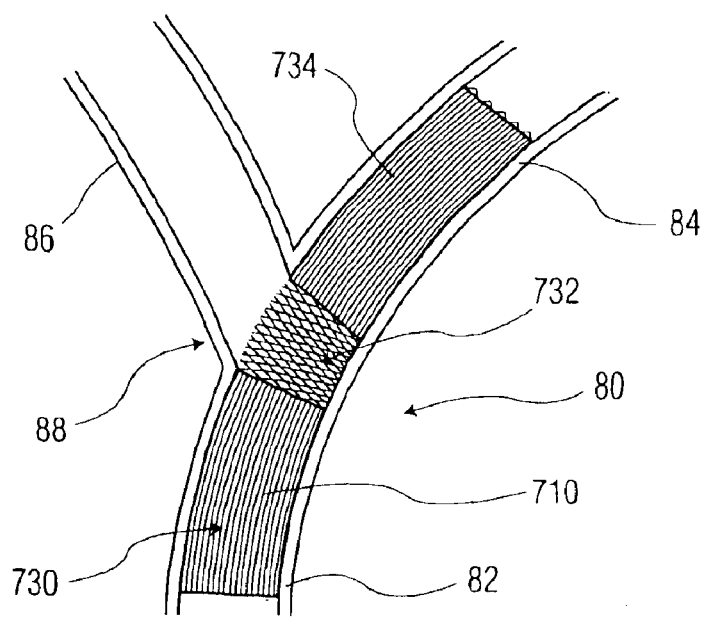
FIG. 12 is an illustration of the stent-graft shown in FIG. 11 after implantation in the portion of the carotid artery shown in FIG. 10.

Stent-graft 710 can be mounted on a delivery device in a manner similar to stent 10 described above. Similarly, the assembled device is inserted percutaneously into the femoral, brachial or radial artery and positioned and deployed like that of stent 10 described above. FIG. 12 is an illustration of the stent-graft 710 implanted into the portion of the carotid artery 80 shown in FIG. 10. As shown, upstream section 730 is located at and engaged with the common carotid artery 82 immediately upstream from the branch 88. Branch section 732 is located at the branch 88 and extends across the location at which the external carotid artery 86 opens into the common carotid artery 82. The downstream section 734 of the stent-graft 710 is located at and engaged with the internal carotid artery 84 immediately downstream from the branch 88. Sections 730 and 734 of the stent-graft 710 function as blood flow-shunting lumens to supplement the functionality of the portions of the arteries 82 and 84, respectively, in which they are implanted. The relatively high porosity branch section 732, however, allows a portion of the blood flow through the common carotid artery 82 to flow into the external carotid artery 86. Stent-graft 710 thereby effectively functions as a pseudobifurcated device.

Figure 13:
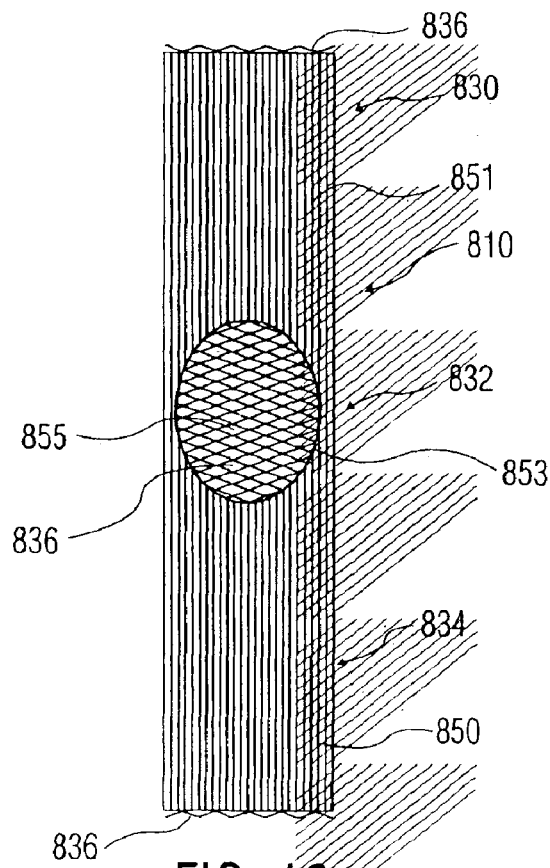
FIG. 13 is an illustration of a stent-graft in accordance with an eighth embodiment of the present invention.

Stent-graft 810, an eighth embodiment of the present invention, is illustrated in FIG. 13. Upstream section 830, branch section 832 and downstream section 834 are similar in structure and characteristics to those of stent-graft 710 described above, and are indicated by like reference numbers. Stent-graft 810 can be implanted in a manner similar to that of stent-graft 710 described above. A primary difference between stent-grafts 710 and 810 is that branch section 832 of stent-graft 810 includes a graft cover portion 853 with an aperture 855. In the embodiment shown, graft cover portion 853 is a section of a unitary graft cover which also includes portions 850 and 851 on the down stream section 834 and upstream section 830, respectively, of the stent-graft 810. Stent-graft 810 can be implanted in a manner similar to that of stent-graft 710 described above, with the aperture 855 aligned with the intersection of the common carotid artery 82 and either the internal or external carotid artery 84 or 86, respectively, to function as a pseudobifurcated device.

Stents and stent-grafts in accordance with the present invention offer a number of important advantages. They have the potential to be highly efficacious, especially in severely diseased aortas and carotid arteries that may not otherwise be capable of receiving conventional stents or stent-grafts. They can be manufactured so as to have selected ones of a wide range of characteristics, thereby enhancing the range of indications for which they can be used. The self-expanding properties of the devices provides a structure that is dynamically compliant. The stent and stent-graft can therefore expand and contract with fluctuations in the diameter of the vessels, in which they are implanted. Stress shielding of the host tissue and associated complications such as degeneration and necrosis can thereby, be reduced with respect to that caused by balloon expandable or other relatively rigid devices. The dynamic compliance also enables the device to change diameter over time with the vessel. For example, if the aneurysmal disease spreads to the fixation section of the vessel, the self-expanding device can continue to conform to the shape of the vessel wall. In contrast, rigid devices will remain at a fixed diameter and may not continue to engage the more recently diseased vessel portions. The self-expanding nature of the device also allows it to be reconstrained and repositioned by a development device. Since accurate placement of the device can be challenging, the ability to reposition the device enhances its usefulness.

Although the present invention has been described with reference to preferred embodiments, those skilled in the art will recognize that changes can be made in form and detail without departing spirit and scope of the invention.

What is claimed is:

1. An implantable medical device for treating a section of a patient's vessel having a vessel branch, a relatively healthy first vessel portion on a first side of the vessel branch, and a diseased vessel portion on a second side of the vessel branch, including:
    a fixation section having a first porosity;
    a diseased section having a second porosity and a diseased section length; and
    a branch section comprising a supportive structure having a third porosity which is greater than the second porosity and a branch section length which is less than said diseased section length.

2. The implantable medical device of claim 1 wherein the branch section includes a plurality of filaments extending between the fixation section and the diseased section.

3. The implantable medical device of claim 2 wherein the filaments of the branch section are helically wound in a braided configuration to form a tubular, radially compressible and self-expandable structure.

4. The implantable medical device of claim 2 wherein a free state diameter of the fixation section is equal to a free state diameter of the branch section.

5. The implantable medical device of claim 2 wherein a radial pressure of the fixation section is greater than a radial pressure of the branch section.

6. The implantable medical device of claim 1 wherein the radial pressure of the fixation section is greater than a radial pressure of the diseased section.

7. The implantable medical device of claim 1 wherein the third porosity is greater than the first porosity.

8. An implantable medical device for treating a section of a patient's vessel having a vessel branch, a relatively healthy first vessel portion on a first side of the vessel branch, and a diseased vessel portion on a second side of the vessel branch, including:
    a fixation section comprising a plurality of filaments which are helically wound in a braided configuration to form a tubular, radially compressible and self-expandable structure having a first porosity, a diseased section comprising a plurality of filaments which are helically wound in a braided configuration to form a tubular, radially compressible and self-expandable structure having a second porosity, said diseased section having a diseased section length and a branch section comprising a supportive, radially compressible and expandable structure having a third porosity which is greater than the second porosity, and a branch section length which is less than said diseased section length.

9. The implantable medical device of claim 8 wherein the branch section includes a plurality of filaments extending between the fixation section and the diseased section.

10. The implantable medical device of claim 9 wherein the filaments of the branch section are helically wound in a braided configuration to form a tubular, radially compressible and self-expandable structure.

11. The implantable medical device of claim 9 wherein a free state diameter of the fixation section is equal to a free state diameter of the branch section.

12. The implantable medical device of claim 9 wherein a radial pressure of the fixation section is greater than a radial pressure of the branch section.

13. The implantable medical device of claim 8 wherein the radial pressure of the fixation section is greater than a radial pressure of the diseased section.

14. The implantable medical device of claim 8 wherein the third porosity is greater than the first porosity.

15. An implantable medical device for treating a section of a patient's vessel having a vessel branch, a relatively healthy first vessel portion on a first side of the vessel branch, and a diseased vessel portion on a second side of the vessel branch, including:

a fixation section having a first porosity;

a diseased section having a second porosity; and a branch section comprising a supportive structure having a third porosity which is greater than the second porosity;

wherein a radial pressure of the fixation section is greater than a radial pressure of the diseased section.

16. An implantable medical device for treating a section of a patient's vessel having a vessel branch, a relatively healthy first vessel portion on a first side of the vessel branch, and a diseased vessel portion on a second side of the vessel branch, including:

a fixation section comprising a plurality of filaments which are helically wound in a braided configuration to form a tubular, radially compressible and self-expandable structure having a first porosity, a diseased section comprising a plurality of filaments which are helically wound in a braided configuration to form a tubular, radially compressible and self-expandable structure having a second porosity, and a branch section comprising a supportive, radially compressible and expandable structure having a third porosity which is greater than the second porosity;

wherein a radial pressure of the fixation section is greater than a radial pressure of the diseased section.

* * * * *